(12) United States Patent
Levin et al.

(10) Patent No.: US 8,524,944 B2
(45) Date of Patent: Sep. 3, 2013

(54) PROCESS FOR THE PREPARATION OF SODIUM GAMMA-HYDROXYBUTYRATE

(75) Inventors: Daniel Levin, La Canada, CA (US); James Luchi, Upland, CA (US)

(73) Assignee: Norac Pharma, Azusa, CA (US)

( * ) Notice: Subject to any disclaimer, the term of this patent is extended or adjusted under 35 U.S.C. 154(b) by 361 days.

(21) Appl. No.: 12/988,026

(22) PCT Filed: Apr. 15, 2009

(86) PCT No.: PCT/US2009/040727
§ 371 (c)(1),
(2), (4) Date: Oct. 15, 2010

(87) PCT Pub. No.: WO2009/129350
PCT Pub. Date: Oct. 22, 2009

(65) Prior Publication Data
US 2011/0028551 A1 Feb. 3, 2011

Related U.S. Application Data

(60) Provisional application No. 61/045,135, filed on Apr. 15, 2008.

(51) Int. Cl.
*C07C 59/01* (2006.01)
(52) U.S. Cl.
USPC .................................................... 562/579
(58) Field of Classification Search
None
See application file for complete search history.

(56) References Cited

U.S. PATENT DOCUMENTS
2007/0270491 A1 11/2007 Cook et al.

FOREIGN PATENT DOCUMENTS
WO 2006124609 11/2006

OTHER PUBLICATIONS

La Cioliono et al., The chemical interconversion of GHB and GBL; forensic issues and implications, Journal of Forensic Sciences, 1315-1323, 2001.
Peterson, Birgitta, Utveckling av en LC-MS-metod for analys av gamma-hydroxibutyrat, gamma-butyrolakton, 1,4-butandiol, amfetamin och metadon, Jun. 1, 2007 (abstract in English).
Page et al., "An Interactive Lesson in Acid/Base and Pro-Drug Chemistry Using Sodium Gamma-Hydroxybutyrate and Commercial Test Coasters", American Journal of Pharmaceutical Education, 2007; 71(3) Article 54.
Kim, Su Mi; PCT International Search Report, Korean Intellectual Property Office, Oct. 22, 2009; p. 1-3; Korea.

*Primary Examiner* — Yevegeny Valenrod

(57) ABSTRACT

The present invention is directed to a process for the preparation of the saponification products of lactones, preferably three- to eight-membered lactones. The present invention is also directed to a process for the preparation of compounds having general formula (I): wherein M is selected from the group consisting of cationic species, preferably metal cations (even more preferably Na), from a compound having the formula (II): comprising reacting a compound having formula (II) with a suitable hydroxide salt (M-OH) (III) such as, preferably, sodium hydroxide, in an aqueous medium. The reaction preferably utilizes a continuous process method for the substantial consumption of reagent and continuous, semi-continuous, and/or batch-wise processing for final consumption of reagent.

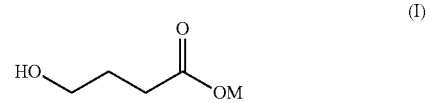

(I)

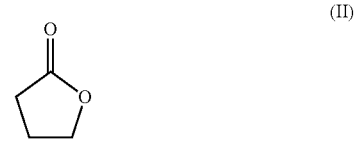

(II)

27 Claims, 3 Drawing Sheets

PROCESS FOR THE PREPARATION OF SODIUM GAMMA-HYDROXYBUTYRATE

CROSS REFERENCE TO RELATED APPLICATIONS

This application is a National Phase application of International Patent Application No. PCT/US09/040,727, filed Apr. 15, 2009, which claims priority to U.S. Provisional Patent Application No. 61/045,135, filed Apr. 15, 2008, the disclosures of each of which are incorporated herein by reference in their entirety.

BACKGROUND OF THE INVENTION—FIELD OF INVENTION

The present invention relates generally to a process for the preparation of sodium gamma-hydroxybutyrate (NaGHB) of general formula (I):

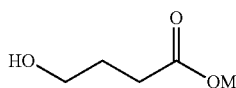

(I)

where M is as hereinafter defined, from gamma-butyrolactone (GBL) (II):

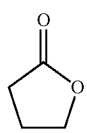

(II)

and a hydroxide source (M-OH) The present invention is also directed to an aqueous concentrate (with a pH of about 8 to about 10 and concentration greater than that of the final formulated drug product) of NaGHB drug substance (for formulation into a pharmaceutical drug product) which is produced in high yields in a continuous and/or continuous/batchwise reaction system. More generally, the present invention relates to a process for the saponification of lactones, especially three- to eight-membered ring lactones (IV):

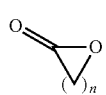

(IV)

n = 1 to 6 for producing pharmaceutically acceptable salt species of general formula (I) and the even more general formula (V).

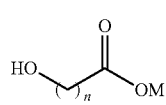

(V)

n = 1 to 6

BACKGROUND OF THE INVENTION

This invention relates to a process for the production of sodium gamma-hydroxybutyrate, also known as NaGHB. The process may occur entirely in a continuous manner or may incorporate a combination of continuous and batchwise processing steps, wherein any batchwise steps are preferably used towards the end of the process. NaGHB and gamma-hydroxybutyric acid (GHBA, wherein the salt M-GHB may be referred to as 'the salt of GHBA') have a number of therapeutic uses including use as a general anesthetic, a hypnotic and treatment of alcohol withdrawal. These compounds are also FDA approved to reduce the number of cataplexy attacks in patients with narcolepsy. NaGHB, also known as sodium oxybate and the trade name XYREM®, is typically delivered as an oral solution containing about 0.5 g/mL NaGHB with a dosage range from 4.5 g/night to 9 g/night.

The process of the current invention is characterized by reacting equimolar or near equimolar amounts of (a) gamma-butyrolactone (GBL) and (b) sodium hydroxide (NaOH) and/or other hydroxides, in the presence of (c) solvent, e.g., water and/or water mixtures such as combinations of water and water-miscible solvents. Water-miscible solvents include, for example, acetonitrile (MeCN), acetone and alcohols. A continuous process may be used for the entire reaction or a continuous process may be used for the substantial conversion of starting material into product. A substantial conversion is defined such that at least 80% of either GBL or hydroxide is converted to product, by-product, degraded, or is otherwise removed from the reaction medium. For example, if one gram of GBL is used as starting material, a substantial conversion has occurred when only one/tenth of a gram or less remains in the reaction medium. Also, for example, if one/tenth or more of the starting hydroxide remains, a substantial conversion has nonetheless occurred if one/tenth or less of GBL remains and vice-versa.

When a continuous process is not used for the entire reaction, the reaction may be finished, i.e. further driven to completion, by utilizing a continuous, semi-continuous, or batch-wise finishing step or steps. The reaction is finished when no appreciable amount of starting material converts to product as determined by any analytical method known in the art, e.g., chromatography or spectrometric analysis. Preferably, at least about 90% conversion of starting material to product occurs prior to any finishing steps. Most preferably, at least about 95 to 99% or more of starting material is consumed prior to any finishing steps. The process provides the saponification products of lactones, particularly three- to eight-membered ring lactones.

The preparation of the sodium salt of gamma-hydroxybutyrate (GHBA, wherein the salt is NaGHB) was first described in 1874 (Annalen, v. 171, p. 258). Typical batch-wise methods of preparation of NaGHB from GBL included refluxing aqueous solutions of GBL for several hours in the presence of a base, such as NaOH (JAGS 1929, v. 51, p. 260). Because the preparation of NaGHB in moderate yields appears from the literature to require the utilization of extended reaction times on the order of hours, the short residence time inherent with continuous processing would not be expected to provide a superior method of producing NaGHB. A superior method would provide pure NaGHB in shorter time, with lower energy expenditure, better throughput per unit volume, i.e. better volume productivity, and in excellent yields along with any and all other advantages that can be realized via continuous processing methods. Until now, such a method has not been achieved.

Early U.S. Pat. No. 3,051,619 (Aug. 28, 1962) describes the preparation and therapeutic compositions of NaGHB. The process occurs in a batchwise manner and involves the heating of an aqueous mixture of GBL and alkali metal base. Additional steps include a recrystallization step from 95% alcohol.

German Pat. Nos. DD 237,308-237,310 (May 15, 1985) also describe the batchwise synthesis of NaGHB in water or water/alcohol mixtures with aqueous sodium hydroxide under prolonged heating (3 to 7 hours). While the use of alcohol/water mixtures allows product to be isolated as a solid from the reaction mixture without an additional recrystallization step, less than quantitative yield of product precipitates from the reaction medium, the product requires an alcohol wash, and additional product is only isolated upon evaporation/distillation of the mother liquor. Accordingly, the batch-process requires numerous steps and while product quality is increased through recrystallization, there is a concomitant loss in product yield.

Therefore, prior art batch-wise production of GHB salts typically require prolonged heating times on the order of hours. (See German Patent Nos. 237,308-237,310; JACS 1929, v. 51 p. 260). Based on such teachings, the use of a continuous process would not be expected to be feasible, let alone be expected to provide superior quality product and yield, without an unreasonably long residence time in the reactor system. Surprisingly and advantageously, the present invention enables a continuous process, despite established and documented batch-wise production methods suggesting the contrary.

The present invention and embodiments thereof resolve the deficiencies of the prior art and provide several distinct and surprising advantages. A first advantage is the rapid and high-yielding production of NaGHB, which utilizes continuous processing for the substantial conversion of reagents to NaGHB product. Additionally, NaGHB is provided in a form suitable for further pharmaceutical processing. The present invention diminishes or eliminates unreacted reagents and formation of by-product(s), thereby increasing the quality of product. Also, the process provides a stable aqueous concentrate of product and is also readily adaptable for production of a solid isolate.

It has also been discovered that utilization of the herein enabled process provides unusually improved reaction characteristics. With the use of equimolar or near equimolar concentrations of reagent, the product is formed in high yield and with superior quality such that total reaction mass isolation is feasible and low-yielding crystallization is not required for product isolation. Further, the process provides such results despite shorter reaction times and lower reaction temperatures. Also, the process eliminates reactor size limitations implicit with batchwise processing, thereby providing quality product in hereto-unrecognized yield and overall volumetric productivity.

As stated above, the current process provides unexpectedly superior quality product. As a result, the present invention discloses that the product crystallization steps which were previously required in the batch-wise production of product can be eliminated for example in generating an aqueous concentrate form of the drug substance. The elimination of such additional steps facilitated by the high purity of the product obtained by the continuous processing method described herein provides the surprising result of near quantitative yields of product as may be generated in the aqueous concentrate form of the drug substance suitable for direct formulation to drug product without drug substance isolation, a hitherto unrecognized achievement for the production of GHB salts.

The elimination of processing steps and the utilization of the presently enabled method of continuous process reaction also provides the synergistic effect of reducing environmental impact and waste production. Furthermore, because NaGHB is a DEA-controlled Schedule 1 drug, the waste minimization associated with continuous processing and total reaction mass isolation by concentration, rather than partial isolation by crystallization, also provides a dramatically improved process. Because the process reduces or totally eliminates waste production, the logistical complications associated with disposal of waste streams containing Schedule 1 material are reduced or even eliminated.

Finally, the present process is unusually adaptable. It is applicable to the processing of other lactones and esters with any number of alkaline, alkaline earth metal hydroxides or other bases including, without limit: potassium, calcium, lithium, barium hydroxides, radio-labeled hydroxides, tetramethylammonium and other "organic" hydroxides, bases formed in-situ such as, for example, the hydroxides formed by reaction of Na or other alkali metals with water or water/alcohol mixtures, or those formed from the quenching of hydrides such as sodium hydride.

It is to be noted that the process advantageously also allows the utilization of other solvents. For example, it is contemplated that mixtures of water and other water-miscible solvents such as MeCN, acetone, and alcohols may be used.

BRIEF DESCRIPTION OF THE DRAWINGS

So that the manner in which the above-recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

BRIEF DESCRIPTION OF REFERENCE NUMERALS

Figure 1:
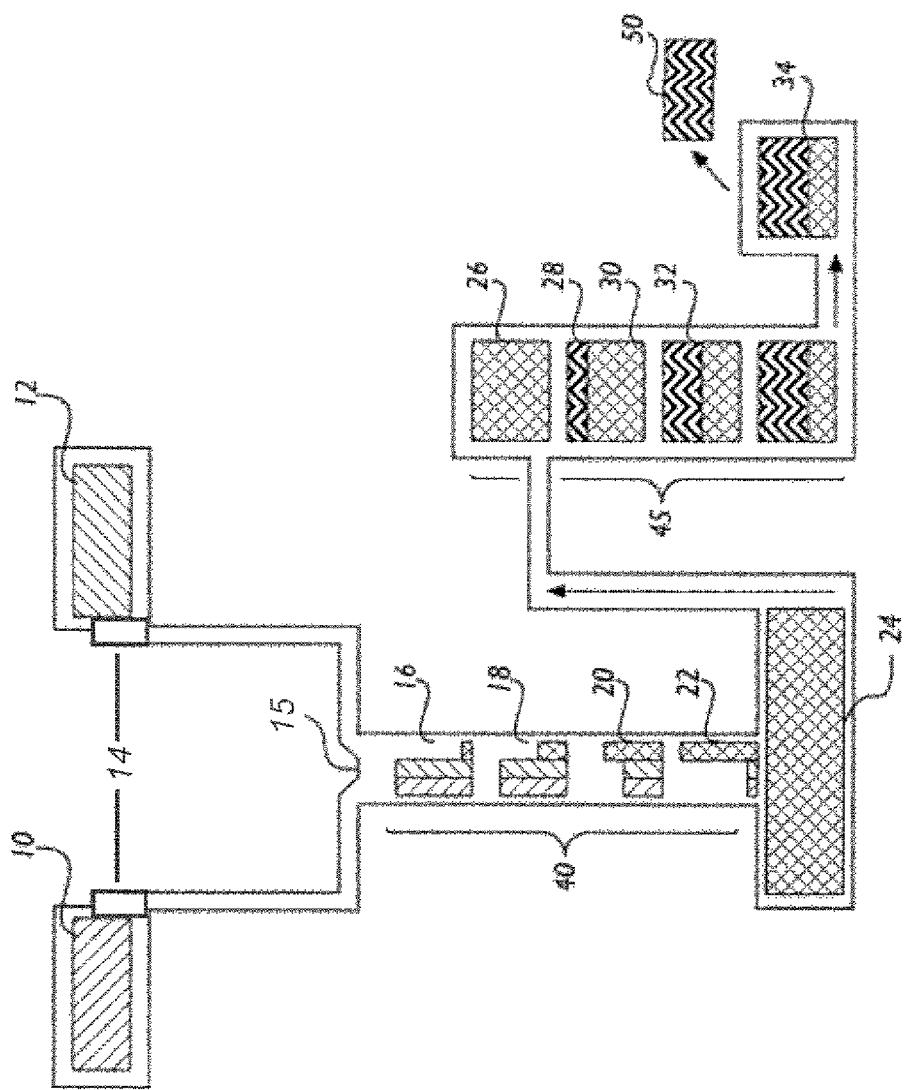
FIG. 1 is a diagrammatic representation of one embodiment of the present invention comprising the continuous process method.

10 GBL; 12 Aqueous (Aq.) Base; 14 Pump; 15 Mixing Chamber (Optional); 16 Segment 1—GBL/Aq. Base/GHB salt; 18 Segment 2—GBL/Aq. Base/GHB salt; 20 Segment 3—GBL/Aq. Base/GHB salt; 22 Segment 4—GBL/Aq. Base/GHB salt; 24 Aq. GHB salt; 26 Aq. GHB salt undergoing concentration; 28 GHB salt; 30 Aq. Medium; 32 Concentrated GHB salt in medium; 34 Aq. Conc. GHB salt; 40 Tube; 45 Concentrating Means; 50 Dried GHB salt; 60 Stirring Means; 62 Temperature Gauge; 64 Reactor; 100 Spray Nozzle (atomizer) with a compressed gas source; 102 Feed Solution; 104 Location of Intake Air Filter; 106 Outlet/Aspirator; 108 Heating Element; 110 Drying Chamber; 112 Inlet temperature sensor; 114 Outlet temperature sensor; 118

Location of Outlet Filter; and 120 Cyclone for solid product isolation with collection vessel; and 122 Pump.

SUMMARY OF THE INVENTION

The present invention is, in one or more embodiments, a process for the preparation of the saponification products of lactones, in particular three- to eight-membered lactones. The process occurs predominantly in a continuous production manner. In some embodiments, the reaction may occur entirely in a continuous process. In other embodiments, the reaction occurs substantially in a continuous process. Additional continuous, semi-continuous, and/or batch-wise processing steps may be incorporated at any point in the process. Preferably, a substantial conversion of starting material to product occurs and then an additional batch-wise step or steps is utilized to convert remaining starting material to product.

The present invention is also, in one or more embodiments, a process for the preparation of compounds having general formula (I):

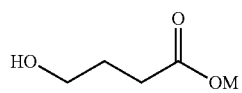
(I)

or more generally the formula (V):

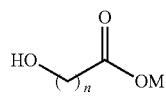
(V)

n = 1 to 6 wherein M is selected from the group consisting of cationic species, such as metal cations (most preferably Na), from a compound having the formula (II):

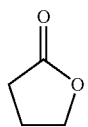
(II)

or more generally the formula (IV):

(IV)

n = 1 to 6 comprising reacting a compound having formula (II) or more generally (IV) with a suitable hydroxide salt (M-OH) (III) such as, preferably, sodium hydroxide, in an aqueous medium. Other cation, counterion species are contemplated, including preferably metal cations, such as the alkalis, alkaline earths, the transition metals, and even radioisotopes thereof. Even more preferably, the metal cations of Ca, Mg, and K can be used in the present invention. Mixtures of metal cations are also contemplated.

The present invention is further directed to a compound prepared according to any one of the processes described herein including products comprising salt(s) of GHBA in aqueous media wherein the GHB salts are present in concentrations either up to the crystallization or precipitation point of the GHB salts in aqueous media or past this point in the form of a supersaturated solution or slurry while maintaining the mobility of the liquid or slurry.

DEFINITIONS

Certain terms of art are used in the specification that are to be accorded their generally accepted meaning within the relevant art; however, in instances where a specific definition is provided, the specific definition shall control. Any ambiguity is to be resolved in a manner that is consistent and least restrictive with the scope of the invention. No unnecessary limitations are to be construed into the terms beyond those that are explicitly defined. The following terms are hereby defined:

As used herein, the term SAPONIFICATION generally refers to the alkaline hydrolysis of an ester, including the alkaline hydrolysis of lactones, to form an alcohol and the salt of a carboxylic acid. Lactones, such as GBL, are cyclic esters. Reference to an ester or to a lactone is a reference to a molecule containing an ester or a lactone group respectively. Such a molecule may also contain other functional groups, including, but not limited to, additional esters and lactones.

As used herein, the term RESIDENCE TIME shall mean the average amount of time a particle of reactant or reactants spends within the reactor.

DETAILED DESCRIPTION OF THE INVENTION

The present invention comprises the introduction of approximately equimolar amounts of GBL (as an aqueous solution or neat liquid) and NaOH (as an aqueous or aq. alcoholic solution) into a mixing chamber, tube, or other device that may function as a reactor. The following reaction scheme demonstrates one embodiment of the present invention:

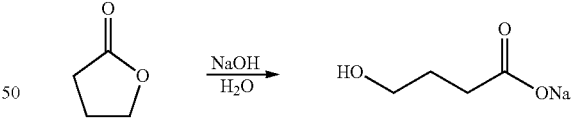

While an aqueous system comprising NaOH/H2O is described above, it will be appreciated that other solvent systems, particularly aqueous mixtures of water and/or water-miscible solvents are usable. Water is one highly preferred solvent system.

The feed solutions may be introduced directly into the continuous reactor or they may pass through a mixing chamber prior to entering the main body of the continuous reactor. This optional mixing chamber may be a simple union where the feed solutions meet with passive mixing before passing into the main body of the reactor. In the case of passive mixing, the mixing chamber may include static mixing elements to increase mixing efficiency with or without turbulence being introduced. The mixing chamber may provide active, dynamic mixing in the form of a powered agitator.

Active mixing in the form of high-shear agitation is contemplated, including the use of an STT® (Spinning Tube-in-Tube), Synthatron™ or other high-shear mixer/reactor systems as described in the literature. Hampton, P. D., Whealon, M. D., Roberts, L. M., Yaeger, A. A., Boydson, R., Organic Process Research & Development (2008), 12, 946-949; Organic Process Research & Development (2009), 13, 64-66; Patents and Patent Applications: U.S. Pat. No. 7,125,527, WO2005/025732 (also US2006/0286015), WO2004/025260, U.S. Pat. No. 6,752,529, U.S. Pat. No. 7,165,881, US2003/0043690. Active mixing of the reactants would further increase mixing and reaction efficiency. The mixing device may be jacketed to control the temperature of the process mixture as it moves through the mixing chamber.

After the point at which the two feed solutions are introduced to one another, one or more—optionally, independently jacketed, insulated and/or otherwise temperature controlled—segments may be installed along the length of the reactor such that each zone can be maintained at a different temperature depending on the process requirements. One unique advantage this confers on the process would be maintaining the early segments of the reactor at low temperature to minimize the formation of impurities at high GBL and or NaOH (starting material) concentrations, while maintaining later segments at higher temperatures to push the reaction to completion.

The process stream is then fed directly into an overflow or other reactor where it is allowed to equilibrate. This step may be continuously, semi-continuously, or batchwise operated. The pH of the reaction mixture is maintained (using titration with GBL or hydroxide) within an alkaline range at a controlled temperature between 0 and 100° C. Preferably, the pH range is from about 8 to about 12, more preferably within about one pH unit of about pH 9.

In a preferred embodiment, the input materials will be titrated such that an exact 1:1 molar ratio of GBL to NaOH is fed into the reaction system and further pH adjustment of the reaction mixture will not be necessary. A pH that is too acidic decreases conversion of starting material into product and a pH that is too alkaline increases formation of impurities and the presence of undesirable amounts of M-OH in the final product.

The nature of the conversion of GBL and NaOH into NaGHB is one of equilibrium between the various species in the reaction mixture, specifically water, GBL, Na+, H+, —OH, GHBA, and NaGHB in the case of NaGHB production from GBL. The relative concentrations of each of these species are dependent on various properties of the solution such as overall and relative concentrations, temperature, pH, and ionic strength, as well as the kinetic and thermodynamic parameters for the inter-conversion between the species. While all species are theoretically present under all conditions, certain species are present in abundance over others within certain ranges of these parameters. For example, under acidic conditions (pH<about 4), H+ concentration is high, which results in high GBL levels as NaGHB is protonated to GHBA and converted to GBL via acid catalysis. Under basic conditions (pH>about 8), —OH concentration is high, driving the equilibrium towards NaGHB via alkaline hydrolysis of GBL. Under neutral conditions (pH about 6 to about 8) and near the range of the pKa of GHBA (about 4.7), a mixture of the various species exists, with constant inter-conversion amongst the various species in solution. As a result, in the reaction mixture and indeed even in the aqueous concentrate form of the product, which ideally will be within about one pH unit of about pH 9, GBL will exist at some level of concentration whether measurable or not. For example, GBL levels of up to 1.0 mol % relative to NaGHB have been observed in aqueous NaGHB solutions at a pH of up to about 9. Even if the dry, solid form of NaGHB (shown to be essentially free of GBL) is dissolved in water and allowed to equilibrate, GBL will eventually be detected in that same solution. The amount of GBL observed is a function of the pH of the aqueous solution, whether or not the pH has been independently adjusted, as also dictated by the nature of the solution (e.g. ionic strength, temperature) and the kinetic and thermodynamic properties of GBL/GHBA/NaGHB system. In other words, in order to obtain NaGHB that is substantially free of GBL, one must either (a) obtain dried product where the GBL has been removed via crystallization or evaporation of the volatiles, including GBL; or (b) adjust the pH to extremely basic levels (pH>11), where degradation of the product solution has been observed over time.

If a slight excess of one reagent over the other is used (intentionally or otherwise), the contents of the overflow or other reactor can be titrated with additional dilute, aqueous NaOH or GBL, if necessary, such that the resulting process stream is of the desired pH. Other options for pH adjustment include injection of dilute aqueous NaOH or GBL at points along the reactor train prior to or in place of the overflow or other reactor.

The pH adjusted process stream can be converted to either a concentrated aqueous solution or solid, including dry solids and/or powders, by one of the methods described below. Production of the aqueous concentrate is the preferred route for the production of NaGHB drug substance prior to formulation into drug product.

With reference to FIG. 1, one possible, exemplary embodiment of the present invention is demonstrated. Feedstock solutions containing GHBA (10) and an aqueous base (12) may be fed, as by a pump (14) (such as a peristaltic pump) either directly into a tube, elongated device, device or chamber (40) or optionally first through a mixing chamber or device (15). Such a device or devices may contain mixing components, either active or static, which intimately mix the reagents. Such a device or devices may even contain a high-shear mixer or reactor, such as an STT® (Spinning Tube-in-Tube), Synthatron™, or similar type of high-shear mixing device. As the mixture passes through the device or unit (40), reagents (10 & 12) react to form the product mixture (24). As can be seen in the figure, conversion of starting material to product increases as the residence time of the mixture increases in the unit (40).

In one embodiment, the unit (40) is an elongated tube comprising a static helical mixing device. Further, the elongated tube may comprise jacketed heating segments. Advantageously, as the mixture passes from segment to segment (16→18→20→22), the segments may be temperature controlled. A low initial reaction temperature in segment one (16) minimizes by-product formation. In later segments, higher reaction temperatures may be used. Higher temperatures in later segments help drive the reaction to completion, thereby reducing the residence time in the reactor and increasing the overall throughput of the continuous reactor system (24). Such temperature gradients are not necessary to produce high yields of product, but can be used to decrease overall residence time in the unit (40). Product mixture (24) may reside in an overflow or other reactor. At this point, the reaction mixture may be adjusted, such as by titration, to regulate pH or reactant concentration. The processed mixture then travels to a concentrator (45) such as, for example, a wiped-film evaporator. The GHB salt concentration increases during evaporation, i.e. low relative concentrations of GHB salt (28) in the aqueous medium (30) increase to provide a more concentrated mixture (32) and then a final concentrated mixture (34). The concentrated mixture (34) optionally may be further concentrated to provide the dry or substantially dry salt of GHBA (50). Alternatively, spray drying or other drying means may also be used.

Figure 2:
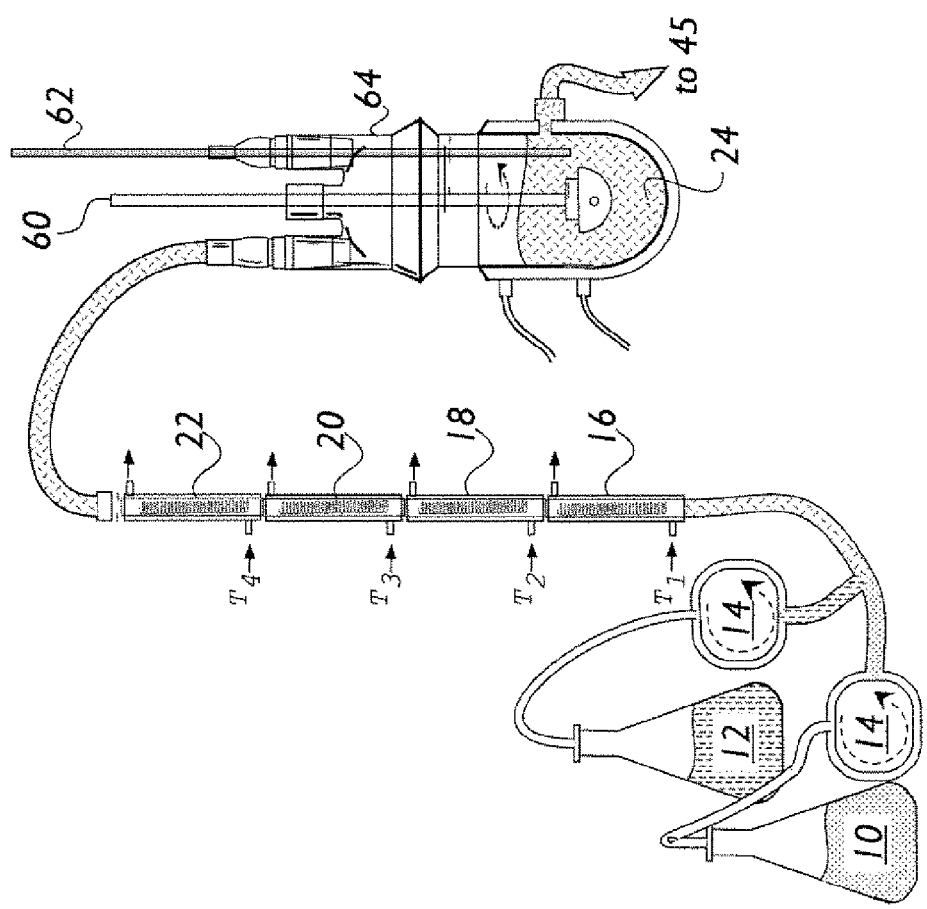
FIG. 2 presents a schematic representation of one embodiment of the present invention demonstrating one possible reactor system setup.

With respect to FIG. 2, one reactor system set-up is demonstrated. Feedstock solutions containing GHBA (10) and an aqueous base (12) may be fed, as by peristaltic pumps (14, 14) into a column containing jacketed (or otherwise temperature controlled) segments (16, 18, 20, 22). In one embodiment, there may be only three such segments, in which the first segment through which the feedstock solution passes contains a mixer, such as a helical mixer, and in which the first segment is jacketed and maintained at about 0-5° C. The second segment contains a helical mixer and may be maintained at about room temperature such as by feeding tap water through the jacket. A third segment may also contain a helical mixer and may be heated to around 50° C. Additional or fewer segments are also contemplated and each individual segment may be maintained at various temperatures, although earlier segments are preferably cooler relative to later segments. Finally, the intimately mixed product may be directed to a jacketed reactor containing stirring means (60), temperature gauges (62), and the product mixture (24). The reactor can allow for final titrations or product adjustment and the mixture can optionally be directed onward, such as to concentration means (45), if so desired.

It is to be noted that the continuous process of the present invention can be performed, for example, in at least one reactor, wherein the reactants are continuously fed into the reactor and the product continuously exits the reactor. Examples of reactor designs that could be applied to this process include, but are not limited to: (a) continuous stirred tank or overflow reactor or cascaded series of reactors, where the reactants are fed into the reactor and the product stream is removed from the reactor at the same rate; (b) continuous or plug flow reactors, where the reagents are continuously fed into a tube or other enclosure containing a mixing device and the product stream flows out of the other end of the enclosure; or (c) any combination of the above. In addition, any of the contemplated reactor designs can include or feed into a batch-wise reactor if desired. The preferred design will involve a combination of a continuous flow reactor feeding into an overflow reactor due to the nature of the lactone ring opening reaction.

It is further to be noted that the optional mixing chamber (15) and/or the entire continuous reactor (40) can be embodied in a high-shear continuous reactor, such as a STT® (Spinning Tube-in-Tube), Synthatron™, or other high shear dynamic mixing device.

Said reaction can be described in two stages: (a) stage one, occurring in a continuous flow reactor, where relatively fast kinetics and high concentrations of both reagents result in high conversion of starting material into product; and (b) stage two, occurring in an overflow reactor, where the bimolecular and equilibrium nature of the reaction combined with low starting material concentrations at high conversion translate into a slower reaction rate, resulting in longer residence times which can be accommodated in an overflow-type reactor. Alternatively, the single or multiple-pass wiped-film evaporator used to remove water from the final aqueous NaGHB solution can also be used to simultaneously drive the reaction to completion as a result of the heat applied to the process stream during water removal.

Because of the dynamic nature of the reaction kinetics, a preferred embodiment of the invention involves utilizing a continuous process for the substantial conversion of starting material to product which occurs in stage one of the reaction and semi-continuous or batch-wise methods for the conversion of starting material to product occurring at stage two. The latter stage provides a superior method for reaction completion when the observed rate of the reaction has decreased.

Suitable reaction temperatures for the saponification of GBL to NaGHB include a gradient temperature of about 0° C. to 50° C., for time periods preferably up to about 2 hours. Alternatively, the initial mixing of GBL with NaOH can be maintained at an initial temperature of about 50° C. for up to about 2 hours. A total feed rate of at least about 40 mL/min at an NaGHB production rate of about 2.2 kg/h is preferable but not limiting, with the feed rate being infinitely scalable to suit reactor size and desired throughput.

In one embodiment, the entire system, including feed systems as well as the reactors, is purged with inert gas. Some examples of inert gas suitable for this purpose include compounds such as nitrogen, helium, neon, argon, etc. Nitrogen is a particularly preferred inert gas for the present invention when an oxygen-free environment is desired.

A person of skill in the art will appreciate that the above descriptions are exemplary. Other physical instrumentalities for operating the reaction in a continuous process are contemplated and include the use of one or more reactors. Such reactors/reactor systems may comprise reactors such as a continuous stirred tank reactor (CSTR), a plug flow reactor, a tower reactor, a cascade-overflow reactor system, a high-shear reactor (such as an STT® (Spinning Tube-in-Tube), Synthatron™, or other high-shear device) or preferably tubing. Preferably, reactors adapted or adaptable for use in continuous processes are used. The reaction, when operated in a two-stage manner, whereby the continuous process is combined with semi-continuous or batchwise methods, can also be operated utilizing a variety of physical instrumentalities. Such instruments include round-bottoms, flasks, cylinders, and other devices used for batch-wise processing. Any instrument usable for the continuous process may be adapted for use in a semi-continuous or batch-wise manner and vice-versa.

Methods of Additional Processing

Wiped-Film Evaporation—The process stream from the reactor can be fed directly into a wiped-film evaporator to yield the concentrated aqueous solution form of the NaGHB product.

Spray Drying—The process stream from the reactor can be fed directly into a spray dryer to yield the solid form of the NaGHB product. It is also possible to spray dry the process stream before pH adjustment and obtain material of the desired quality.

Freeze Drying—The process stream from the reactor can be lyophilized to obtain a solid. The product may comprise granules or nodules that can be ground or milled for formulation.

Azeotropic Drying—The process stream from the reactor can be dried to a solid by using water miscible solvents with a high water content azeotrope such as isopropanol. Distillation, with or without cosolvents, may be used to facilitate drying.

The above list of drying and evaporation methods is exemplary; other methods that provide for drying or concentrating of final product are contemplated. It is to be noted that the processing method used and the conditions under which the processing occur may help determine the final morphology and purity of the final product. For example, it is well understood that the final solid product may exist as a dry solid or may retain some measure of solvent depending on the extent of concentration or drying. Alternatively, for example, the final product may comprise a powder or granules or other physical forms depending on the processing methods used.

Examples

Standard Batch Process (Comparative).

The prior art teaches that a mixture of 16.3 g of gamma-butyrolactone (0.19 eq, 86.1 MW) and 7.4 g of sodium hydroxide (0.19 eq, 40 MW) dissolved in 30 cc of water was boiled under a reflux condenser for about three hours. At the end of this time more water was added to dissolve the salt and the solution was filtered and evaporated to dryness under reduced pressure. The salt was recrystallized from alcohol. The yield was 11.5 g (40% of the theoretical amount). (JACS 1929, v. 51, p. 260).

Preparation of One-Kilogram of NaGHB as an Aqueous Concentrate.

The procedure described below was used to prepare a one-kilogram sample of NaGHB as an aqueous concentrate.

The following solutions were prepared as feedstock for the continuous reactor: GBL Feedstock Solution—GBL (751.0 g, about 670.5 mL, 8.723 mol) was diluted to 1200 mL with reagent grade water and mixed until homogeneous (clear, colorless); NaOH Feedstock Solution—NaOH (51 wt % in H2O, 677.4 g, about 447.1 mL, 8.637 mol, 0.99 equiv) was diluted to 1200 mL with reagent grade water and mixed until homogeneous (clear, colorless).

Both feed solutions were fed through a peristaltic pump at equal flow rates of 21 ml/min through 1.6 mm ID tubing. The two feed solutions were then combined through a union into a 24-inch long static mixing device (PP/LDPE, ID=8 mm) at a total combined feed rate of 42 ml/min. In this particular instance, a helical-type static mixer within a tube is used, but other static or dynamic mixing devices, including high-shear mixing devices, would be equally effective. The intimately mixed solutions from the outlet of the static mixer are then fed through a 36-inch long tube (PTFE, ID=3/16") and into a glass receiving vessel.

Example of Batch-Wise Processing Following Continuous Processing

In order to produce the concentrated aqueous solution of NaGHB and to finalize the reaction, the following method was employed: Once all of the feedstock solution had been processed, the resulting clear, colorless to straw yellow solution was allowed to equilibrate overnight with stirring. The pH was then adjusted with dilute aqueous NaOH until stable overnight at pH 8.9 at ambient temperature. The product solution was then concentrated from about 40 wt % to about 60 wt % in vacuo.

The solution of NaGHB was then filtered through a medium (40-60 micron) fritted glass funnel and packaged. The resulting aqueous concentrate met or exceeded 99% purity as measured by GC analysis of the bis-TMS derivative of the final product.

Production of Solid Form of NaGHB

Figure 3:
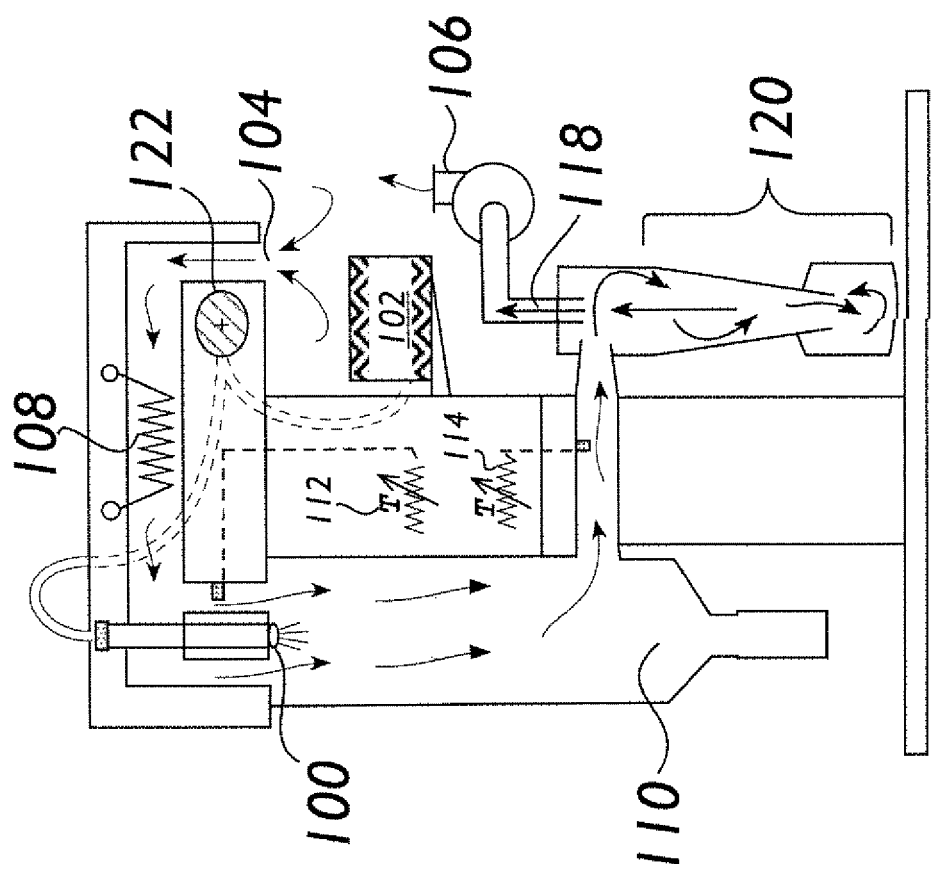
FIG. 3 is a cross-sectional view of one exemplary spray-drying device demonstrating its principle of operation.

One preferred method of producing dried product according to the present invention comprises the use of spray drying. FIG. 3 demonstrates one embodiment of a spray-drying device for producing dried product, which comprises a spray nozzle (atomizer) with a compressed gas source 100. This component may optionally comprise a jacket cooling and nozzle de-clogging assembly. Component 102 is a vessel containing the aqueous product, which is fed, via pump, to the spray nozzle at 100 for atomization. Component 104 represents the location of the intake air filter (not shown). As seen, gas (which may be air or nitrogen) is drawn into the aperture through 104 prior to reaching heating element 108. Inlet temperature sensor 112 and outlet temperature sensor 114 monitor the temperature of the heated gas being fed into the drying chamber and the dry product stream exiting the drying chamber, respectively. Drying occurs in drying chamber 110. A cyclone with attached product collection chamber is found at 120. After passing through the chamber, the feed is filtered at or about 118 before the filtered feed, now comprising air, nitrogen or other gas, reaches outlet/aspirator 106. A detailed description of the operation of these elements is now given.

The aspirator motor/fan assembly at the terminal end of the spray dryer pulls air (or an inert gas, such as nitrogen) through the filter at the intake end of the unit. The air is passed over a heating coil before being drawn into the drying chamber. At the same time, the feed pump draws the solution of material to be spray dried from the feed vessel and feeds it into the spray nozzle, where it is atomized with compressed air into the drying chamber and mixed with the heated air being supplied by the aspirator fan. Evaporation of the volatile components of the feed solution is effected by the heat from the aspirator-supplied air and the vast increase in surface area resulting from the atomization. The dry material then passes from the drying chamber to the cyclone for collection by centripetal force and gravity. Fines or particles that are below the collection threshold determined by the spray drying parameters and cyclone geometry are then carried out of the cyclone and filtered out of the air stream before reaching the aspirator.

It has been discovered that the key parameters that need to be balanced for the successful application of spray drying to this process are as follows: Feed concentration; Feed diluent; Feed rate; Feed temperature; Spray nozzle type; Spray nozzle compressed air pressure; Aspirator flow rate (hot air supply); Inlet air temperature (hot air into drying chamber); Outlet air temperature (temperature between drying chamber and cyclone); and Cyclone and drying chamber design/geometry.

Application of spray drying technology to the isolation of a dry solid form of NaGHB led to the identification of one set of parameters listed below using a Büchi B-190 lab-scale spray dryer. The following parameters are exemplary; other parameters and systems of spray-drying may be used. In order to produce the dry powder form of NaGHB, the reaction solution (without pH adjustment or concentration) was processed using the following conditions:

Feed concentration: 30-40 wt % NaGHB; Feed diluent: water (process stream from continuous reactor); Feed rate: Setting 3; Feed temperature: RT; Spray nozzle type: Concentric pressure spray atomizer; Spray nozzle pressure/flow rate: 68 psi/450 L/h; Aspirator flow rate: Setting #8; Inlet air temperature: 150±5° C. (Setting 9); Outlet air temperature: 100-105° C.; Cyclone/drying chamber design/geometry: Büchi B-190 Design.

Processing the reaction solution in this way resulted in a 16% yield of a solid NaGHB. Typical yields for spray drying are 20-40%, and are dependent on the nature of the product being dried as well as the solvent being removed. Product loss is mostly due to material adhering to the surface of the interior surfaces of the spray dryer. Accordingly, it is expected that the total yield from spray drying according to this or similar methods will be high if product is recovered from the spray drying apparatus or if product disposal within the device is minimized. The quality of the NaGHB isolated by spray drying using the above parameters was higher than the reference material obtained in >99% purity.

Production of NaGHB in a Continuous Process through Concentration.

The process stream from the static mixer/reactor tubing will be fed into an overflow reactor, where the pH will be adjusted to the desired level with aqueous sodium hydroxide.

The process stream from the outlet of the overflow reactor will then be fed directly into a wiped-film evaporator, where it will be stripped of water to the correct NaGHB concentration. The output from the wiped-film evaporator comprises the final product. The process can be operated in a truly continuous manner, wherein the process output from the continuous reactor (via an equilibration vessel as necessary) can be fed directly and immediately into the wiped-film evaporator, or in a batchwise manner where the entire process output from the continuous reactor is fed into a holding tank for equilibration prior to concentration and/or further processing.

Analysis of NaGHB by Ion-Chromatography

Analysis for NaGHB is typically accomplished using techniques such as HPLC or GC/GC-MS. The primary application of these methods in the literature is for the detection of trace amounts of NaGHB, GHBA, and GBL in beverages and bodily fluids for forensic investigations. The unique challenges associated with supplying NaGHB as an aqueous concentrate rather than the usual dry white solid form along with the inherent dynamic pH-dependent equilibrium between NaGHB, GHBA, and GBL in aqueous media requires a different approach to analytical method development: purity or assay analysis of NaGHB by HPLC with UV detection is not ideal; the only chromophore present is the weak carboxylate (e.g. the $\lambda_{max}$ for sodium acetate is reported at 200 nm with an $\epsilon_{max}$ of 50). Furthermore, most organic compounds absorb at or near 200 nm to some extent. As a result, impurities that absorb strongly in this UV region could have a disproportionate effect relative to their actual molar or weight percent abundance in either the purity or assay analyses.

To deal with these issues, the use of CAD (Charged Aerosol Detection) with HPLC was investigated. The CAD detector responds to all non-volatile and most semi-volatile analytes, requiring the use of mobile phase mixtures with volatile components similar to those used in HPLC-MS applications. While CAD detection results in a much higher response to NaGHB as compared to UV detection, other limitations of HPLC for NaGHB analysis become apparent. Specifically, the pH of the mobile phase in conjunction with the pH-dependent nature of the equilibrium between NaGHB, GHBA, and GBL results in severe tailing of the analyte peak and irreproducible results under a wide range of conditions.

The application of ion chromatography (IC) on the other hand, has been applied successfully to the assay of NaGHB content in the aqueous concentrate. Typically, IC is used to detect and quantify small amounts of anion (e.g. halide ions) and cation (alkaline and alkaline earth ions) impurities or detect stoichiometric amounts of similar ions in the analysis of the salt forms of drug substances. For the analysis of salts such as sodium acetate and NaGHB, both the anion and cation can be assayed separately. For reference, IC uses ion exchange resin as a stationary phase and aqueous mobile phases of varying ionic strength (isocratic or gradient) to influence the stationary phase retention and ultimate chromatographic separation of various ions. Examples of ionic strength modifiers for anion IC include sodium hydroxide and potassium hydroxide.

Specifically for NaGHB, it has now been determined that IC can be used to assay the gamma-hydroxybutyrate (GHBA) anion content of aqueous concentrate samples of NaGHB. Since only the anion is detected, excess sodium cation from pH adjustment of the aqueous concentrate does not interfere with the analysis. In addition, the mobile phase pH is always basic (pH>10) which controls the NaGHB/GHBA/GBL equilibrium on a timescale sufficient to allow for accurate and precise analyses. The mobile phase can also be used as the diluent to further mitigate this equilibrium issue.

As a result, IC has been successfully applied to assay NaGHB content in the aqueous concentrate drug substance formed according to the present invention.

Purity analysis can be accomplished by the removal of water from the aqueous concentrate by lyophilization or azeotrope with isopropanol to obtain a dry solid. The trimethylsilyl (TMS) derivative of the dry NaGHB is then formed and analyzed by GC or GCMS.

CONCLUSION

In the foregoing description, certain terms and visual depictions are used to illustrate the preferred embodiment. However, no unnecessary limitations are to be construed by the terms used or illustrations depicted, beyond what is shown in the prior art, since the terms and illustrations are exemplary only, and are not meant to limit the scope of the present invention. It is further known that other modifications may be made to the present invention, without departing the scope of the invention, as noted in the appended claims.

We claim:

1. A process for the saponification of a compound comprising a lactone to produce a reaction product, wherein said process comprises the steps of continuously reacting the reagents: about one equivalent of a lactone; and about one equivalent of an aqueous base; by
    mixing said lactone with said aqueous base to form a mixture,
    optionally titrating said mixture to ensure an equimolar ratio of reactants,
    optionally adjusting the pH of said mixture by addition of reactant, and
    concentrating said mixture.
2. The process of claim 1, wherein the temperature of said mixture is controlled between the freezing point of the process stream and 150° C.
3. The process of claim 2, wherein the temperature of said mixture is controlled between about 0° C. and about 100° C.
4. The process of claim 1 in which the reaction mixture is further processed in a continuous, semi-continuous, and/or batch-wise manner after substantial consumption of any reagent.
5. The process of claim 4 wherein the further processing comprises batch-wise processing after at least about 90% consumption of any reagent.
6. The process of claim 1 wherein said mixture is concentrated to between about 40% by weight to about 60% by weight of said reaction product to produce an aqueous concentrate form of the compound.
7. The process of claim 1 wherein said mixture is concentrated by use of a spray-dryer to solid form.
8. The process of claim 1 wherein said compound comprises a lactone having three, four, five, six, seven or eight members of general formula (IV):

n = 1 to 6

9. The process of claim 1, wherein the pH of said mixture is adjusted to within the range of about 8 to about 10.

10. The process of claim 1 wherein the pH of said mixture is adjusted to about 9.

11. A process for the formation of a compound having general formula (I):

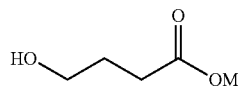

by alkaline hydrolysis of a compound having formula (II):

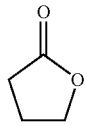

comprising continuously reacting about one equivalent of compound (II); and about one equivalent of an aqueous base having, a formula of M-OH (III), wherein M is a cationic species; by mixing said compound (II) with said aqueous base (III) to form a mixture, optionally titrating said mixture to ensure an equimolar ratio of reactants, optionally adjusting the pH of said mixture by addition of reactant, optionally processing the reaction in a continuous, semi-continuous, or batch-wise manner after substantial consumption of (II) and/or (III), and concentrating said mixture.

12. The process of claim 11, wherein said compound (II) is evaporatively isolated and optionally crystallized.

13. The process of claim 11, wherein said compound (II) is crystallized.

14. The process for the formation of a compound having general formula (I):

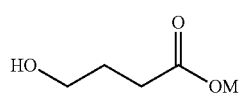

wherein M is Na, by alkaline hydrolysis of a compound having formula (II):

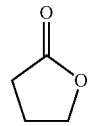

comprising continuously reacting about one equivalent of compound (II); and about one equivalent of an aqueous base having a formula of Na—OH (III); by
mixing said compound (II) with said aqueous base (III) to form a mixture,
optionally titrating said mixture to ensure an equimolar ratio of reactants,
optionally adjusting the pH of said mixture by addition of reactant,
optionally processing the reaction in a continuous, semi-continuous, or batch-wise manner after substantial consumption of (II) and/or (III), and concentrating said mixture.

15. The process of claim 14 wherein said mixture is concentrated to between about 40% by weight to about 60% by weight of the compound of formula (I) to produce an aqueous concentrate form of the compound.

16. The process of claim 15 wherein said mixture is concentrated by a concentration means to a solid form.

17. The process of claim 16 wherein said concentration means is selected from the group consisting of spray-drying, freeze drying (lyophilization), and azeotropic drying.

18. The process of claim 14 wherein said mixture is substantially dried to produce a dry product comprising compound of formula (I).

19. The process of claim 14 wherein said mixture is titrated to a pH within the range of about 8 to about 10.

20. The process of claim 14 wherein said mixture is titrated to a pH of about 9.

21. The process of claim 14 wherein said compound (II) is evaporatively isolated and optionally crystallized.

22. The process of claim 14 wherein said compound (II) is crystallized.

23. The process of claim 1, wherein the two reactants are mixed in a mixing device and then introduced into a continuous reactor.

24. The process of claim 23 wherein the mixing device is a passive mixing device.

25. The process of claim 24 wherein the passive mixing device is selected from the group consisting of a laminar flow mixing device and an in-line static mixing device.

26. The process of claim 23 wherein the mixing device is an active mixing device.

27. The process of claim 26 wherein the active mixing device is selected from the group consisting of a powered agitation mixing device, a high-shear mixing device, and a high shear reactor.

* * * * *